(12) United States Patent
Jensen et al.

(10) Patent No.: US 7,110,124 B2
(45) Date of Patent: Sep. 19, 2006

(54) METHOD AND APPARATUS FOR OBTAINING GEOMETRICAL DATA RELATING TO A CANAL

(75) Inventors: Preben Damgård Jensen, Birkerød (DK); Tom Olesen, Gørløse (DK)

(73) Assignee: Oticon A/S, Smørum (DK)

( * ) Notice: Subject to any disclaimer, the term of this patent is extended or adjusted under 35 U.S.C. 154(b) by 358 days.

(21) Appl. No.: 10/476,583

(22) PCT Filed: May 8, 2002

(86) PCT No.: PCT/DK02/00031

§ 371 (c)(1),
(2), (4) Date: Nov. 19, 2003

(87) PCT Pub. No.: WO02/091913

PCT Pub. Date: Nov. 21, 2002

(65) Prior Publication Data

US 2004/0138590 A1    Jul. 15, 2004

(30) Foreign Application Priority Data

May 17, 2001   (DK) ............................... 2001 00784

(51) Int. Cl.
*G01B 11/00* (2006.01)
*A61B 18/22* (2006.01)
(52) U.S. Cl. ...................... 356/626; 600/117; 600/170; 600/171; 600/182; 600/587
(58) Field of Classification Search ................. None
See application file for complete search history.

(56) References Cited

U.S. PATENT DOCUMENTS 4,281,931 A    8/1981   Chikama
4,694,184 A    9/1987   Pryor
5,045,936 A *  9/1991   Lobb et al. ..................... 348/67
5,784,098 A *  7/1998   Shoji et al. .................. 356/608
6,059,718 A *  5/2000   Taniguchi et al. .......... 600/117
6,485,413 B1 * 11/2002  Boppart et al. ............. 600/160

FOREIGN PATENT DOCUMENTS

EP      0 352 952 A2  *  1/1990
JP      11-295618 A   * 10/1999

* cited by examiner

*Primary Examiner*—Gregory J. Toesley, Jr.
*Assistant Examiner*—Juan D. Valentin, II
(74) *Attorney, Agent, or Firm*—Dykema Gossett PLLC

(57) ABSTRACT

The invention uses light to determine the distance from the tip of a probe to the internal wall of the canal, and based on the position of the probe, this information is used to generate information about the shape of the canal. Light with a first and a second wavelength range is directed onto a semi-transparent mirror surface at the distal portion of the probe. Light in the first wavelength range is reflected from the mirror surface to illuminate a circumferential area of the internal surface of the canal, and light in the second wavelength range is transmitted through the mirror surface to illuminate an area in front of the distal portion of the probe. The received light is analyzed in the first wavelength range to determine the distance from the probe to the internal surface of the canal at points of the circumference, and analyzed in the second wavelength range to determine the distance from the probe to an object in front of the probe. Thereby it is ensured, that the bottom surface of the canal is not touched or injured while the internal surface of the canal is measured.

19 Claims, 3 Drawing Sheets

METHOD AND APPARATUS FOR OBTAINING GEOMETRICAL DATA RELATING TO A CANAL

AREA OF THE INVENTION

The invention relates to a method and an apparatus for obtaining geometrical data relating to the internal surface of a canal. The method and the apparatus are used to gain a data mapping of the internal surface of a canal, so that a 3-dimensional data or digital model of the internal surface of the canal is obtained. In some cases it is important to also obtain information about a bottom surface of the canal. This is especially important when the canal forms part of the human body. In this case the bottom surface may be sensitive, and should not be touched. Also in connection with inspection and measurement of other canals, which are sensitive to contact such as surfaces of newly painted or otherwise surface treated holes the invention may be used and provides an advantage over the prior art.

If the human ear is mapped using the method, the 3-dimension model can be used to produce a shell, which has the exact shape of the ear canal and the shell may form the basis for a ITE or CIC hearing aid or an earmould for use with a BTE hearing aid. Also earmoulds or shells for other purposes such as hearing protection, or for headsets may be produced from the data model. The shell can be produced on the basis of the data model in different ways, such as by recent developed rapid prototyping methods or by well known machining, e.g. in a CNC machining center.

Today hearing aid shells are produced on the basis of an ear impression taken by introducing a semi-fluent material into the ear canal, which is left to cure in the ear. After curing the semi-fluent material becomes elastic and coherent and is pulled out of the ear canal in one piece. A shell is produced on the basis of this ear impression. Having the ear impression taken is associated with discomfort for the patient, and in many cases the resulting shell does not fit the canal very well. Therefor a method and a device is sought whereby a hearing aid shell may be produced without the necessity of taking the ear impression.

The advantage of having a data model of the ear canal is that the production of the shell can take place at any location, which means that hearing aid manufactures may produce the shells at a central production facility. Uniform quality can then be ensured. Further the data model may be transmitted either as it is obtained or right thereafter for evaluation at a production facility. Thereby a data model of the hearing aid, which may be realized based on the geometry and shape of the canal may be generated. The date model of the hearing aid may be transmitted back to the end user for visual evaluation.

BACKGROUND OF THE INVENTION

In the following documents some of the above problems are addressed, but no satisfactory solutions are presented.

U.S. Pat. No. 5,487,012 discloses a method for computer controlled production of an adaptive earpiece comprising at least one part, which is individually matched to the contours of an auditory canal. The method comprise the steps of tracing of the contours of the auditory canal to obtain contour data, digitization of the contour data and storage of the digitized values, converting the digitized values into a multi-dimensional computer model of the external contours of the adaptive earpiece and producing the earpiece on the basis of the computer model. The patent mentions that the tracing of the internal contours of the ear canal may be performed using ultra sound. The document further discloses a method for tracking the ear canal based on the use of an ear impression, but such a method would not resolve the problems relating to the usual way of producing shells as described above.

U.S. Pat. No. 5,056,204. In this document a method for producing a hearing aid, which is worn in the ear is described. The method comprise the steps of initially taking measurements of the inner space of the ear op to the eardrum for use in producing an individual shape of the body member corresponding with the measurements of the inner space of the ear. It is mentioned that the measurement is done by means of a laser. How this actually takes place is not disclosed.

PCT application WO 00/34739 discloses a method for manufacture of a hearing aid shell comprising a motor actuated ultrasonic probe used to acquire the shape data of the ear canal, an image processing computer, which also incorporates the driving electronics for the probe, with an edge detection algorithm used to filter the data. Thereby a digital image file of the three-dimensional topography of the ear canal is obtained. The ultrasonic probe is combined with a fiber optic probe used to monitor the position of the probe within the canal. The fiber optic probe comprises an inner coherent bundle of fibres and an objective lens that relay the image of the canal to a CCD camera and an outer incoherent bundle of fibres that surround the coherent bundle and permits the illumination of the canal by an external light source that is optically coupled to the other end of the incoherent bundle. The position of the probe is determined solely by monitoring the displacement of the probe in one linear direction. Only the possibility of monitoring the motor, which is a step-motor is mentioned for this purpose. The probe is mounted on a stiff rod, and is not capable of following the possible bends of the ear canal. This limits the use of the probe, as many people especially older people have ear canals with sharp bends.

Various methods and apparatuses for determining the internal properties of internal surfaces have been suggested, however none of these are useful when it comes to mapping the internal surface of a canal of the human body, in order to generate a digital model of the interior wall of the canal.

U.S. Pat. No. 5,004,339 discloses an apparatus for determining a characteristic of the inside surface of a bore comprising:

a guided wave fiber optic element capable of insertion into a bore;

a laser light source for directing light onto the proximal end of said fiber optic element;

means for directing light emanating from the distal end of said fiber optic element onto the inside surface of said bore and for directing light reflected from the inside surface of said bore onto the distal end of said fiber optic element; and photo detector means capable of generating an output signal dependent upon light incident thereon;

means for directing light emanating from the proximal end of said fiber optic element onto said photo detector means whereby the output signal of said photo detector provides an indication of a characteristic of an inside surface of a bore. The patent further concerns a method for determining a characteristic of the inside surface of a bore using the above apparatus. The method may be employed on a body passage. Obtaining dimensional information concerning a cylindrical surface is mentioned, but not described in detail. Visualization of the bore wall of a sample is described. The sampled and held output of array video data is fed to the y and z axis of a storage video display with the x axis comprised by a pickoff of the movement along the bore length. No system for generating precise information concerning the position and orientation of the distal end of the fiber optic element is mentioned. The means for directing light from the distal end of the optic element onto the inside surface of the bore may be a mirror surface or a lens such as a wide-angle lens. The mirror surface can be designed to focus light on a point of the bore wall surface which is axially forward of the forwardmost portion of the mirror. This may be used to examine the bottommost portion of a blind bore. The patent does not mention the combined use of a mirror surface and a lens. Also the use of a semi-transparent mirror intended to direct part of the light to the circumferential surface and another part of the light to the surface which is axially forward of the mirror is not mentioned.

U.S. Pat. No. 5,469,245 relates to a method and an apparatus for measuring a three-dimensional position of a surface of a lengthwise object such as a pipe having a uniform cross section from a corresponding two-dimensional observed image of the object surface to measure, for example, the size of a defect in the surface. The patent does not mention systems to determine the exact location and orientation of a probe, which is inserted into the pipe.

U.S. Pat. No. 5,895,927 relates to a method an apparatus for profiling and dimensionalizing an interior cross-sectional portion of a tubular structure. The probe utilizes a disc of unfocused light to illuminate a cross-section of the interior surface and images the illuminated cross-section from the interior surface to a photo detector array, where the image can be evaluated. The photo detector array provides a continuous video signal, which can be fed to a video monitor and to a frame grabber. The resulting array of numbers can be processed by a computer program to find those pixels, which represent the illuminated cross-section, and through this, dimensional (diameter) data may be obtained. The patent does not mention systems for determining the position and orientation of the probe, in order to gain information relating to the length of the tubular structure or relating to possible bends in the tubular structure.

U.S. Pat. No. 6,073,043. This document describes a method and apparatus for determining the position and orientation of a remote object relative to a reference coordinate frame. The method and apparatus includes a plurality of field-generating elements for generating electromagnetic fields and a drive for applying signals to the generating elements. The signals generate a plurality of electromagnetic fields that are distinguishable from one another. The apparatus comprises a remote sensor having one or more field-sensing elements for sensing the fields generated and a processor for processing the outputs of the sensing element (s) into remote object position and orientation relative to the generating element reference coordinate frame. The position and orientation solution is based on the exact formulation of the magnetic field coupling. The system can be used for locating the end of a catheter or endoscope, digitizing objects for computer databases, virtual reality and motion tracking.

SUMMARY OF THE INVENTION

The object of the invention is to provide a method for obtaining geometrical data relating to the internal surface of a canal in order to be able to generate an exact model of the internal surface of the canal. It is an important aspect of the present invention, that during the measurement a bottom wall of the canal is not touched. This is achieved by the method according to claim 1. The invention uses light to determine the distance from the tip of a probe to the internal wall of the canal, and based on the position of the probe, this information is used to generate information about the shape of the canal. Light with a first and a second wavelength range is directed onto a partially reflective and partially transparent surface at the distal portion of the probe. Light in the first wavelength range is reflected from the surface to illuminate at least one point of a circumferential area of the internal surface of the canal, and light in the second wavelength range is transmitted through the surface to illuminate an area in front of the distal portion of the probe. The light reflected from the illuminated areas is received and directed to at least one light sensitive element to generate an output relating to the first and the second wavelength range. The output relating to the first wavelength range is analyzed to determine the distance from the probe to the internal surface of the canal at points of the circumference, and the output relating to the second wavelength range is analyzed to determine the distance from the probe to an object in front of the probe. Thereby it is ensured that the bottom surface of the canal is not touched or injured while the internal surface of the canal is measured. By the use of light to determine the distance between the probe and the surface of the canal, it is easy to locate foreign object in the canal such as hair or earwax, and these objects are left out of the data model. In this way a more precise model is obtained. Further the use of light makes it possible to obtain very precise data, without touching any internal wall part of the canal.

Preferably the light sensitive element is an array of CCD elements.

In an embodiment of the method distance data are obtained and recorded while position data concerning the spatial position and rotation of the distal portion of the probe are obtained and recorded during movement of the probe from a first to a second location. Thereby an operator may map a larger coherent area of the internal surface of the canal in an easy and straightforward way as the data are recorded during operator controlled motion of the probe.

In a further embodiment the probe is flexible, and capable of bending. This has the advantage that the probe is capable of assuming the shape of the canal, which is not straight. This makes it possible to insert and retract the probe the full length of the canal as the probe continually assumes the shape of a bending canal. This aspect of the invention is important, as the ear canal of especially elderly people may have sharp bends, and by using the invention, the probe may be carefully maneuvered past such bends as data are recorded. This can be done without making impressions in the tissue of the ear canal, which might corrupt the measurements.

Foreign objects such as earwax may corrupt the obtained date. In an embodiment of the invention this is avoided by analyzing the light in order to recognize such objects. This may be done by analyzing the output with respect to the spectral composition of the light received at the light sensitive element.

Measurements may be performed while moving the probe either towards or away from the bottom wall of the canal. In an embodiment according to the invention the measurements are performed while moving the probe away from the bottom of the canal. The operator may then place the probe deep in the canal, while taking care that the bottom wall is not touched, and then start the measurements and pull the probe gently out of the canal while taking the measurements.

The probe may either be pulled out by hand, or a guiding mechanism may be provided, to make sure that the probe is moved at a uniform speed.

In an embodiment of the invention the position data are obtained using transdusing means transmitting a magnetic field associated with the distal portion of the probe and second transdusing means detecting the magnetic field generated by the transmitter fixed relative to the head of the patient. The use of this method of obtaining the position data is very precise. Further it is possible to make the measurement noise insensitive. Also the transmitter of the magnetic field may be made small, so that it may easily be build into the tip of the probe.

A further object of the invention is to provide an apparatus for obtaining geometrical data relating to the internal surface of a canal in order to be able to generate an exact model of the internal surface of the canal.

This is achieved with the apparatus according to claim 9.

Claims 10–14 contain advantageous embodiments of the apparatus.

Further advantageous embodiments of the apparatus are contained in claims 15–19

According to the invention the apparatus for obtaining geometrical data relating to the internal surface of a canal comprises:

- a probe having a rod part with a proximal portion and a distal portion and comprising at least one light guide and a light source at the proximal end of the light guide,
- a light emitting distal portion insertable into the canal and having means for directing light containing wavelengths within a first wavelength range and a second wavelength range from the distal end of the light guide onto a surface, whereby
- the surface is arranged to reflect light in the first wavelength range onto at least one point of a circumferential area of the internal surface of the canal, and arranged to transmit light in the second wavelength range to illuminate the area in front of the probe,
- means for receiving the light reflected from the illuminated areas, and means for directing the received light to at least one light sensitive element to generate an output,
- means for analyzing the output relating to the first and the second wavelength range to determine the distance from the probe to the internal surface of the canal at points of the circumference, and to determine the distance to objects in front of the probe.

By using the semi-transparent mirror to simultaneously direct light towards both the circumference and the bottom wall of the canal and analyzing the reflected light, the distance to any objects in front of the probe may be determined. Thereby it is ensured, that the probe does not touch the bottom wall of the canal.

Focusing means in the form of a lens may be inserted in the light path between the light guides and the mirror, to obtain a focused light beam.

Preferably the light sensitive element comprise an array of elements such as CCD elements.

In and advantageous embodiment the light path between the second mirror surface and the CCD element comprises an image guide between the distal end and the proximal end of the probe, and where the light sensitive element is arranged at the proximal end of the probe, and receives the light emitting from the image guide. A flexible image guide is chosen, so that it may bend along with the probe to follow the bends of the ear canal. The advantage is here that no severe space restrictions exists at the proximal end of the probe, and the most suitable light sensitive element may be chosen along with possible lenses, without regard to size.

In and advantageous embodiment at least the first mirror surface is arranged on a transparent body, and comprises a coating, which reflects light in a first wavelength range and which is transparent to light in a second wavelength range and transmits the light in the second wavelength range. The light in the second wavelength range is directed to the area in front of the distal portion of the probe, and the light reflected from any objects in this area is directed through the transparent body and guided towards the light sensitive element. By this arrangement it becomes possible to receive two images at the light sensitive element, one of the circumference of the ear canal, and one of the environment in front of the tip of the probe. The two images will be in each their wavelength range but are captured by one and the same light sensitive element.

Preferably the CCD element is sensitive to light in both the first and the second wavelength range and the first or the second sensitivity range may be selected. Thereby one and the same light sensitive element may be used to capture the two pictures, from the circumference and from the front of the probe.

Control of the light received at the CCD element may be achieved by controlling the light input to the light guide. When the area in front of the probe is to be illuminated, light in the second wavelength range is inputted to the light guide, and when the circumference is to be illuminated, light in the first wavelength is used. Control of the light input to the light guide may be obtained through control of the light source or by the use of filters.

In another embodiment the probe comprises two CCD elements sensitive to each their wavelength range, whereby a mirror having a semitransparent coating is arranged such that one of the light sensitive elements receives the light from the circumference and the other light sensitive element receives the light reflected from the area in front of the distal portion of the probe. In this case the two pictures are available at all times at the two light sensitive elements.

DESCRIPTION OF A PREFERRED EMBODIMENT

Figure 1:
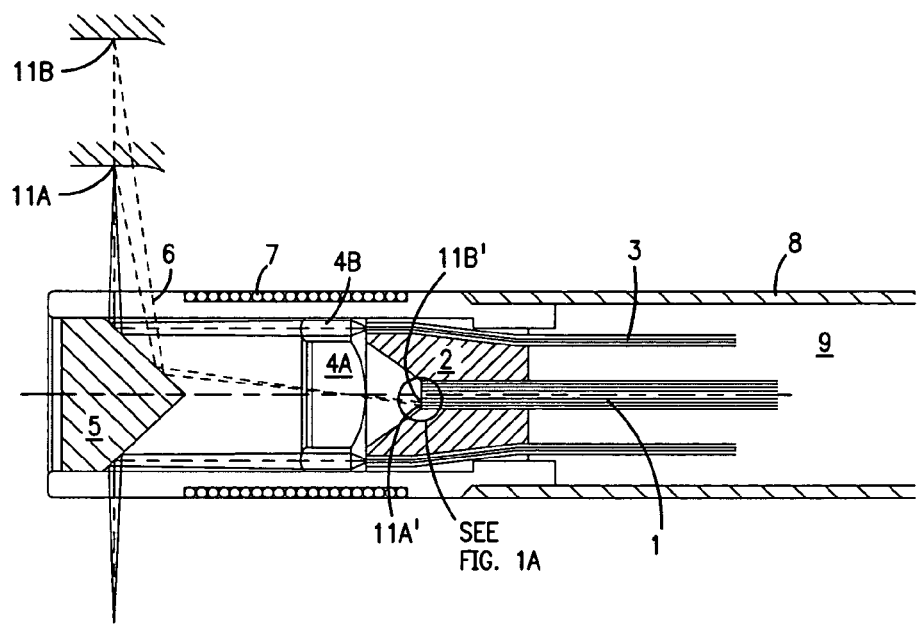
FIG. 1 is a sectional view of a the distal end of a probe showing the light path for determining the distance to the inside wall of a canal.
Figure 1A:
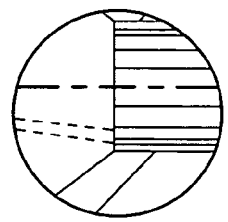
FIG. 1A shows a detail of FIG. 1.

The probe shown in FIG. 1 has a distal light emitting portion and a rod portion 9 connecting the distal portion to a proximal part (not shown). The rod portion 9 comprises a flexible pipe 8 and a set of light guides 3 and an image guide 1. The image guide 1 is placed centrally in the pipe 8, and the light guides 3 are arranged between the pipe 8 and the image guide 1. Near the tip of the probe the light guides 3 are fastened between an inner bushing 2 and an outer tube 6. An annular lens 4B is arranged at the bushing 2 to capture the light emitting from the light guides 3, in order to focus said light. The focused light beam is directed to a first portion of a mirror 5 mounted at the tip of the tube 6. The first portion of the mirror 5 has a circumferential conical plane with a top angle of 45°. Thereby the focused light beam emitted from the lens 4B will be directed in a right angel away from the longitudinal axis of the probe, and towards a surrounding canal wall 11. The tip portion of the tube 6 is made of a transparent material, so that the light may be transmitted freely through the tube wall at the tip.

In FIG. 1 the wall 11 is shown as an example in a first distance at 11A near the tip of the probe and in a second distance 11B farther away from the tip of the probe. Light reflected from the wall at 11A of the canal will enter the tube 6 and be reflected from a second portion of the mirror 5 and enter a second lens 4A. From the lens 4A the light is directed towards the surface of the image guide 1. If light is reflected from a wall part 11B farther away from the probe, it will also be directed towards the surface of the image guide 1, but as can be seen in the enlarged section labeled "5x" this light enters the image guide 1 closer to the center thereof. The second portion of the mirror 5 has a circumferential conical plane, but with a top angle, which may differ from 45°.

The image received on the surface of the image guide 1 is transmitted through the image guide 1, and will appear at the other end thereof. Here the image is captured by a CCD array (not shown). The signal from the CCD is transferred to signal processing unit for further processing in order to calculate the distance from the probe to the canal wall. This is done by a triangulation method well known in the art.

In stead of an image guide 1, it is possible to arrange the CCD array at the distal end of the probe, such that the reflected light is captured at the distal end of the probe. This is a simpler construction, but it requires a CCD element, which is small enough to be mounted at the tip of the probe, which is going to enter the ear canal. The signal from the CCD element in this case is carried in the usual way by wire back to the proximal end of the probe to be analyzed as described to determine the distance to the wall of the ear canal.

In the preferred embodiment a focused light beam is directed towards the wall of the canal, but also unfocused light may be used. The advantage of using focused light is that the focused light provides better contrast and this result in a more precise detection of the distance between the probe and the canal wall.

A single light guide may be used for both directing light to the tip of the probe and for transmitting the reflected light back to the CCD element. But this requires a beamsplitter, and has the disadvantage of a reduced signal to noise ratio, and therefore the separate light guides are preferred.

Figure 2:
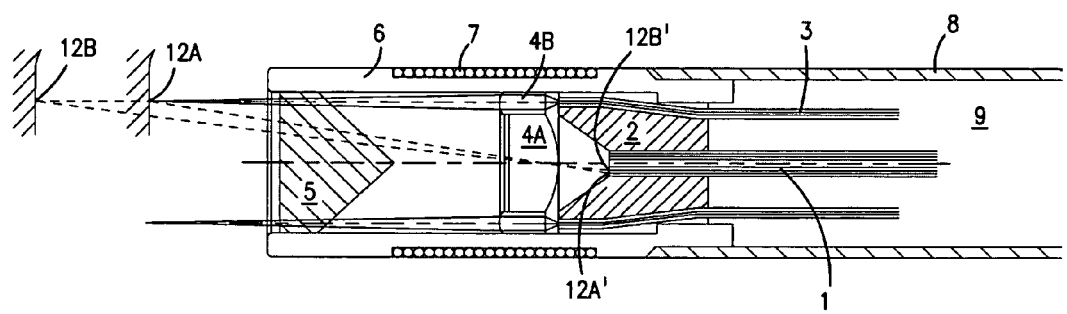
FIG. 2 is a sectional view of the probe in FIG. 1 showing the light path for determining the distance to an object in front of the distal portion of the probe.

In FIG. 2 the light path is shown in a second mode of operation of the probe. The mirror surface 5 is coated with a coating, which in a first wavelength range reflects the light, but which in a second wavelength range transmits the light. The light path of the light in the second wavelength range is shown in FIG. 2. Here light in the second wavelength range emitted from the lens 4B passes through the lens 5 and is reflected from an object 12A, 12B in front of the probe. At 12A and 12B the end wall of the canal is shown at two different distances from the probe. The end wall is the tympanic membrane in case the ear canal is scanned. The reflected light is transmitted through mirror element 5 and through lens 4A and forms an image of the area in front of the probe on the surface of image guide 1. At the proximal end of the image guide the two pictures, namely the front and the circumferential picture, are either led to each their CCD element by the use of a further semitransparent mirror, or led to one and the same CCD element which is chosen so as to be selectively sensitive to the two wavelength ranges.

The semitransparent mirror surface 5 provides another possibility, namely that a conventional picture is captured through this mirror. This is done by using the image guide in the same fashion as in usual endoscobes. Here light in the wavelength range in which the mirror surface is transparent is guided through the image guide from the proximal end thereof to the tip of the probe. Reflected light is transmitted back through the image guide and by means of a beamsplitter directed towards the surface of a CCD. Thereby the CCD may capture a natural image of the objects in front of the probe, and such an image could be valuable for the person conducting an ear scan.

In FIGS. 1 and 2 a coil 7 is shown at the tip of the probe. The coil is used to generate a magnetic field, which is picked up by sensors shown schematically in FIG. 3. At each sensor position A, B and C two or more sensors are located, which are designed to register the magnetic field in each their direction. Through this arrangement the exact location and orientation of the tip of the probe can be determined at any time. In the case shown in FIG. 3, the probe is located inside the canal of a human ear, shown schematically in the figure. The three sensor locations are arranged in a fixed construction, which in use is held immobilized relative to the patient's head. In the embodiment shown in FIG. 3, the fixed construction comprises a tripod, whereby each of the sensor positions are placed at the outer end of each of the branches of the tripod. In use the coil 7 at the probe tip is driven at a fixed frequency and by using a lock-in procedure, any noise coming from other magnetic fields in the surroundings may be cancelled out from the sensor signals.

Using a colour sensitive CCD element has the further advantage that colour information may be used when analyzing the light reflected from the surface of an ear canal. If white light is used, it is possible to determine the relative content of red, green and blue light in the received signal, and thereby foreign objects such as earwax may be identified. This is because earwax will reflect the light in other wavelength ranges than the naked skin of the ear canal. If the semitransparent mirror option described above is employed this will cause some restrictions as to how detailed the colour information is, as only a limited range of wavelengths may be reflected from the mirror surface 5. In the generated data model any lump of earwax may be left out, and the data for the particular surface of the ear canal may be generated through extrapolation using the data from the surrounding wall parts.

In the described embodiment only one coil is located at the tip of the probe, and the coil is aligned with the length axis of the probe. This means that rotational movement of the probe about its length axis cannot be detected by measuring the magnetic field. It is suggested according to the invention, that the probe is made rotationally rigid, so that if the proximal end of the probe is retained and prevented from rotation about the length axis, then the distal end cannot rotate either. In this way only 3 different position and 2 different rotational parameters must be obtained to fully locate the probe in the canal.

In use the probe is gently inserted into the ear, and the magnetic sensors are placed in close relation to the patient's head. Placing the probe in the ear is done while objects in front of the probe are monitored as described through the semi transparent mirror. The picture captured this way is displayed on a monitor, so that the operator may know when the probe is approaching the tympanic membrane. Once the region near the tympanic membrane is reached, the measurements may commence. This is done while retracting the probe as corresponding values of the distances to the canal wall and the position of the probe are recorded. The recording is continued until the probe reaches the outer regions of the outer ear.

Figure 3:
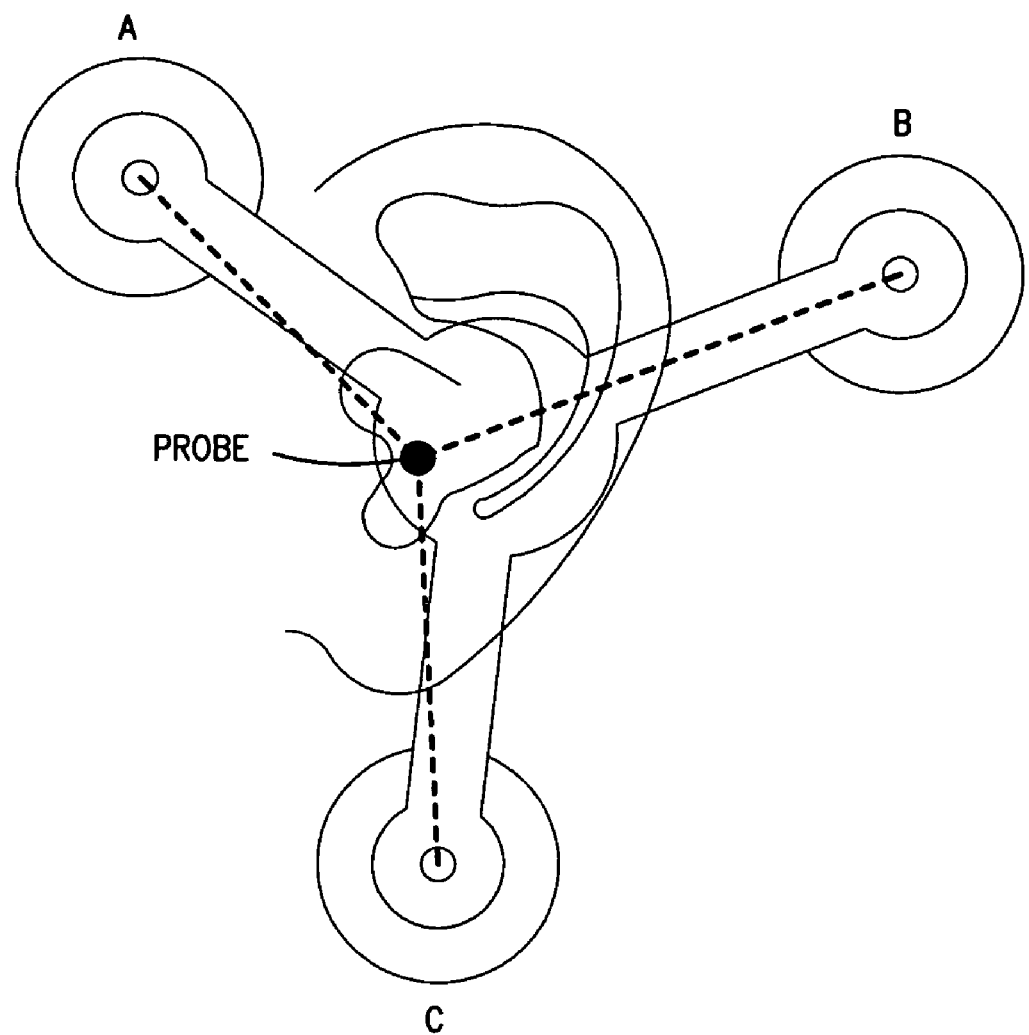
FIG. 3 is a side view showing the human ear and the arrangement of the position sensors.

A guiding arrangement for the probe may be located at the tripod shown in FIG. 3. A guiding arrangement may comprise two or more opposite flat rollers between which the probe is to pass. By slightly squeezing the probe between the rollers, rotational movement of the probe around the length direction is prevented. Such a guiding mechanism may however be implemented in many different ways, and it is not shown in the figures or described in more detail.

The invention claimed is:

1. A method for obtaining geometrical data relating to the internal surface of a canal whereby a probe having a light emitting distal portion is inserted into the canal, the method further comprising the steps of:
   directing light with wavelengths within a first and a second range onto a partially reflective and partially transparent surface at the distal portion of the probe,
   reflecting light in the first wavelength range from the surface to illuminate at least one point of a circumferential area of the internal surface of the canal, and transmitting light in the second wavelength range through the surface to illuminate an area in front of the distal portion of the probe,
   receiving the light reflected from the illuminated areas, and directing the received light to at least one light sensitive element to generate an output relating to the first and the second wavelength range,
   analyzing the output relating to the light in the first wavelength range to determine the distance from the probe to the internal surface of the canal at points of the circumference, and analyzing the output relating to the light in the second wavelength range to determine the distance from the probe to an object in front of the probe.

2. A method as claimed in claim 1, where distance data are obtained while position data concerning the spatial position and rotation of the distal portion of the probe are obtained during movement of the probe from a first to a second location.

3. A method as claimed in claim 2, where the probe is flexible and bends in correspondence to the bends of the canal during the movement of the probe from the first to the second location.

4. A method as claimed in claim 1, where the light sensitive element comprise an array of sensitive elements such as CCD elements.

5. A method as claimed in claim 1, where the output is analyzed in order to identify foreign objects on the surface of the canal.

6. A method as claimed in claim 1, where the probe is initially inserted to a position adjacent a bottom wall of the canal and where the geometrical data are obtained during extraction of the probe from the canal.

7. A method as claimed in claim 2, where the position data are obtained using first transducing means associated with the probe transmitting a magnetic field, and second transducing means associated with the head detecting the magnetic field generated by the transmitter at the probe.

8. A method as claimed in claim 1, where the canal is the human ear canal.

9. An apparatus for obtaining geometric data relating to the internal surface of a canal, the apparatus comprising,
   a probe having a rod part with a proximal portion and a distal portion and comprising at least one light guide and a light source at the proximal end of the light guide,
   a light emitting distal portion insertable into the canal and having means for directing light containing wavelengths within a first wavelength range and a second wavelength range from the distal end of the light guide onto a surface, whereby
   the surface is arranged to reflect light in the first wavelength range onto at least one point of a circumferential area of the internal surface of the canal, and arranged to transmit light in the second wavelength range to illuminate the area in front of the probe,
   means for receiving the light reflected from the illuminated areas, and means for directing the received light to at least one light sensitive element to generate an output,
   means for analyzing the output relating to the light in the first and in the second wavelength range to determine the distance from the probe to the internal surface of the canal at points of the circumference, and to determine the distance to objects in front of the probe.

10. An apparatus as claimed in claim 9, wherein the light sensitive element comprises an array of elements such as CCD elements.

11. An apparatus as claimed in claim 9, wherein the apparatus is constructed to obtain and retrieve distance data during motion of the probe from a first location to a second location and where the apparatus comprises means for obtaining position data concerning the spatial position and rotation of the distal end of the probe during the motion of the probe from the first location to the second location.

12. An apparatus as claimed in claim 11, wherein means are provided for generating a data model of the internal surface of the canal on the basis of the retrieved position and distance data.

13. An apparatus as claimed in claim 9, wherein the light source has a wavelength range and the CCD element has a sensitivity range such that foreign objects in the ear canal may be detected and identified through spectral analysis of the light received at the light sensitive element.

14. An apparatus as claimed in claim 11, where the means for obtaining position data regarding the probe comprise transmitting means associated with the distal portion of the probe, and receiving means arranged at fixed positions outside the canal.

15. An apparatus as claimed in claim 14, where the transmitting means comprise a coil generating a magnetic field, and the receiving means comprise magnetic sensitive elements such as hall-elements.

16. An apparatus as claimed in claim 10 where the probe comprises first light guides for transmitting light from the proximal to the distal end of the probe and further comprises a second mirror surface for directing the light reflected from the circumferential surface of the canal towards the CCD element.

17. An apparatus as claimed in claim 16, where the light path between the second mirror surface and the light sensitive element further comprise an image guide between the distal end and the proximal end of the probe, and where the light sensitive element is arranged at the proximal end of the probe, and receives the light emitting from the image guide.

18. An apparatus as claimed in claim 10, where the CCD element is sensitive to light in both the first and the second wavelength range and where the first or the second wavelength range may be selected.

19. An apparatus as claimed in claim 10 where the probe comprises two CCD elements sensitive to each their wavelength range, whereby a second mirror having a semitransparent coating is arranged such that one of the light sensitive elements receives the light from the circumference and the other sensitive element receives the light reflected from the area in front of the distal portion of the probe.

* * * * *